(12) United States Patent
Thiberg

(10) Patent No.: US 6,537,305 B1
(45) Date of Patent: Mar. 25, 2003

(54) DEVICE FOR EXTERNAL TREATMENT OF THE ORAL CAVITY BY MEANS OF LIGHT AND METHOD FOR MEDICAL TREATMENT

(75) Inventor: Rolf Thiberg, Åkersberga (SE)

(73) Assignee: Biolight Patent Holding AB, Danderyd (SE)

(*) Notice: Subject to any disclaimer, the term of this patent is extended or adjusted under 35 U.S.C. 154(b) by 0 days.

(21) Appl. No.: 09/889,212

(22) PCT Filed: Jan. 13, 2000

(86) PCT No.: PCT/SE00/00046
§ 371 (c)(1),
(2), (4) Date: Oct. 17, 2001

(87) PCT Pub. No.: WO00/43069
PCT Pub. Date: Jul. 27, 2000

(30) Foreign Application Priority Data

Jan. 13, 1999 (SE) .............................................. 9900076

(51) Int. Cl.⁷ .............................................. A61B 18/18
(52) U.S. Cl. ............................ 607/89; 606/13; 128/898
(58) Field of Search .................... 606/9, 13; 607/88, 607/89; 128/898

(56) References Cited

U.S. PATENT DOCUMENTS

| | | | | |
|---|---|---|---|---|
| 4,556,064 A | * | 12/1985 | Pomeranz | 607/89 |
| 4,951,663 A | * | 8/1990 | L'Esperance, Jr. | 607/89 |
| 5,500,009 A | | 3/1996 | Mendes et al. | 607/88 |
| 6,063,108 A | * | 5/2000 | Salansky | 607/89 |
| 6,238,424 B1 | * | 5/2001 | Thiberg | 607/89 |
| 6,238,425 B1 | * | 5/2001 | Thiberg | 607/89 |

FOREIGN PATENT DOCUMENTS

SU 746869 7/1980

* cited by examiner

Primary Examiner—David M. Shay
(74) Attorney, Agent, or Firm—Alfred J. Mangels

(57) ABSTRACT

Apparatus and a method for external medical treatment of the oral cavity with the aid of light. A light-emitting device is held against or in the close proximity to a patient's cheek. The device includes light-emitting diodes or corresponding elements that emit infrared (IR) light. A drive arrangement includes a computer and circuits for driving the light-emitting diodes, wherein the computer delivers electric signals to the drive circuits. The drive arrangement causes the light-emitting device to emit infrared light in accordance with a series of pulse repetition frequencies of about 7.8 Hz, followed by light that has a pulse repetition frequency of about 287 Hz, which is followed by light that has a pulse repetition frequency of about 31.2 Hz.

7 Claims, 1 Drawing Sheet

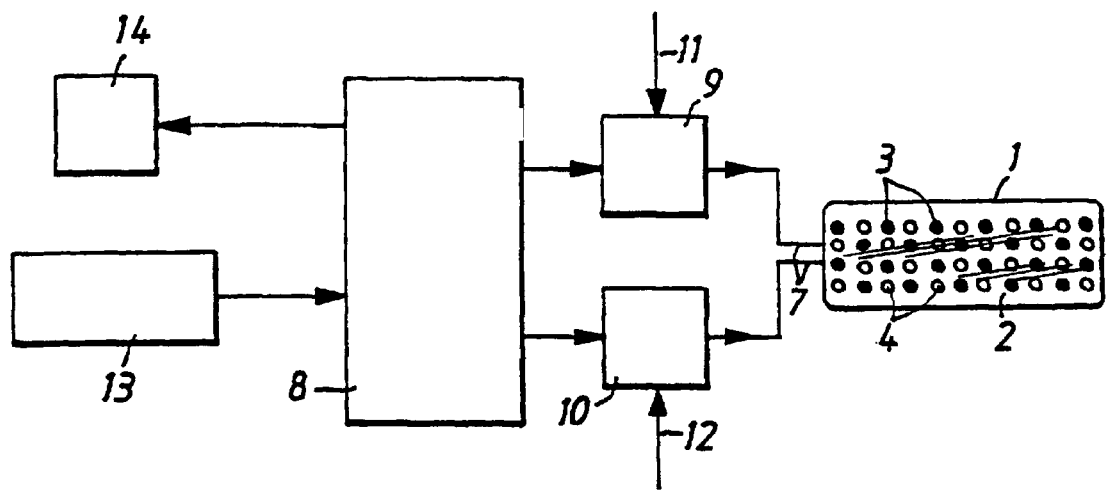
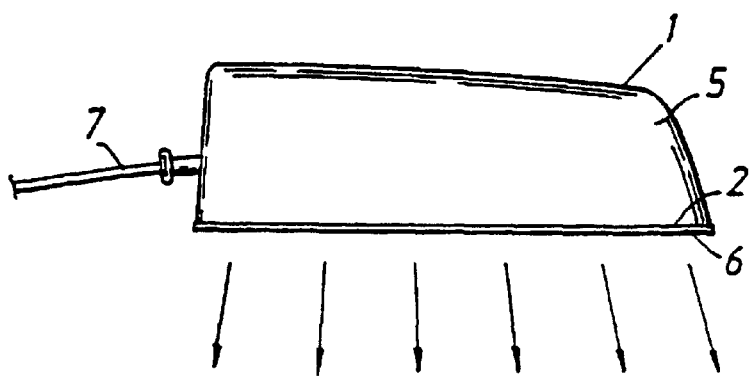

DEVICE FOR EXTERNAL TREATMENT OF THE ORAL CAVITY BY MEANS OF LIGHT AND METHOD FOR MEDICAL TREATMENT

BACKGROUND OF THE INVENTION

1. Field of the Invention

The present invention relates to an apparatus for external medical treatment of the oral cavity with the aid of light, more specifically with the aid of light which palliates- and/or cures different states of diseases, and a method for medical treatment.

2. Description of the Related Art

Swedish Patent Specification No. 502 784 teaches an apparatus for external medical treatment with the aid of light that includes a light-emitting device which is intended to be held against or close to the body of an individual, and drive means for the light-emitting device. The light-emitting device includes light-emitting diodes or corresponding elements which are intended to emit infrared light. According to the aforesaid patent specification, the drive means is adapted to control the light-emitting device to emit infrared light in a first stage and then to emit visible light in a second stage. The drive means is adapted to control the light-emitting device to pulsate the infrared light and the visible light in accordance with a predetermined series of pulse frequencies.

It has also been found that very good results can be obtained when treating a patient with solely one or more types of monochromatic light and with light other than infrared light, such as visible light of different colors emitted in accordance with a given pulse frequency.

It is also known to perform different treatments by using certain specific pulse repetition frequencies to achieve certain effects.

It has thus been found that an apparatus of the aforesaid kind can be used very successfully in treating many different states of diseases and injuries, for instance sports injuries, stretched muscles, muscular pain, joint pain, headaches, various inflammatory conditions, various skin complaints, such as acne, back pains, etc., provided that the light is emitted in a certain way. In this regard, treatment with light has a favorable influence on injury healing processes and will palliate and/or cure various diseases.

There is thus an understanding that treatment with certain light that is emitted in certain frequency series will have a significantly greater effect in shortening the time taken to cure or palliate a disease.

It has surprisingly been found that an apparatus of this kind can be used to palliate and cure gingivitis, i.e. inflammation of the gums, and also pariedontitis, i.e. loosening of the teeth. The present invention relates to apparatus for this purpose.

Further the invention relates to a method for medical external treatment of the oral cavity with the aid of light.

SUMMARY OF THE INVENTION

The present invention thus relates to an apparatus and a method for the external medical treatment of the oral cavity with the aid of light. The apparatus includes a light-emitting device which is intended to be held against or in the close proximity of the patient's body, and drive means for the light-emitting device. The light-emitting device includes light-emitting diodes or corresponding elements adapted to emit monochromatic light and the drive means is adapted to control the light-emitting device to emit at least one type of monochromatic light over one or more predetermined time periods and to pulsate the light emitted in accordance with a predetermined pulse frequency or a series of pulse frequencies over said time periods. The drive means includes a computer and drive circuits for the light-emitting diodes, wherein the computer is adapted to send electric signals to the drive circuits so that the light-emitting diodes function to emit light within predetermined time periods and with predetermined pulse repetition frequencies. The light-emitting device is intended to lie against a patient's cheek. The drive means and the light-emitting device are adapted to emit solely infrared (IR) light in accordance with a series of pulse repetition frequencies, wherein light having a pulse repetition frequency of about 7.8 Hz is emitted first, followed by light that has a pulse repetition frequency of about 287 Hz, followed by light that has a pulse repetition frequency of about 31.2 Hz.

BRIEF DESCRIPTION OF THE DRAWINGS

The invention will now be described in more detail partly with reference to an exemplifying embodiment thereof shown on the accompanying drawing, in which FIG. 1 is a schematic block diagram illustrating an apparatus of the present kind; and FIG. 2 is a side view of a light-emitting device.

DESCRIPTION OF THE PREFERRED EMBODIMENTS

FIGS. 1 and 2 illustrate generally an apparatus for external medical treatment with the aid of light, said apparatus including a light-emitting device 1 which is intended to be held against or in the close proximity of the patient's body. The light-emitting device is shown from one side in FIG. 2 and from beneath in FIG. 1. This device includes a casing 5 which houses a transparent plate 6. Located beneath the plate 6 is a surface 2 on which a plurality of light-emitting diodes 3, 4 or corresponding elements are mounted.

The light-emitting diodes thus emit light through the plate 6 when activated, i.e. when supplied with current through a cable 7. When the device is being used, the casing 5 is held so that the plate 6 will lie against the relevant part of the patient's body.

The apparatus also includes drive means for operating the light-emitting device 1. The drive means is adapted to control the light-emitting device 1 to emit desired types of monochromatic light of different wavelengths over different predetermined time periods, and to pulsate the light emitted in accordance with a predetermined pulse frequency or series of pulse frequencies over said time periods.

The light-emitting device 1 may include light-emitting diodes 3 adapted for the emission of infrared light. These diodes are shown with solid circles in FIG. 1. Visible light can be emitted with the aid of other light-emitting diodes 4. These diodes are illustrated with empty circles in FIG. 1.

The drive means includes a computer 8 which controls drive circuits 9, 10 to which signals for driving the light-emitting diodes are sent from the computer via a conductor.

The computer and the drive circuits are of a suitable known kind. The drive means or computer has connected thereto a keyboard 13 by means of which the operator can key-in data which causes the drive means to activate the light-emitting device in a desired manner. The apparatus will conveniently include a display 14 for displaying the settings entered through the keyboard. This display may be the computer screen.

A major part of the apparatus described above is also described in the aforesaid Swedish patent specification.

According to Swedish Patent Specification No. 9900074-7 at least the drive circuits 9, 10 of the drive means are mounted in the light-emitting device 1.

According to one embodiment of the invention described in this latter patent specification, the computer 8 is integrated with the light-emitting device 1. The computer 8 of this particular embodiment is preferably a microprocessor with associated memory. The computer 8 is programmed to control the light-emitting diodes to effect different treatments, via the drive circuits 9, 10.

Thus, the computer may be separate from the light-emitting device 1, as shown in FIG. 1, or it may be integrated with the light-emitting device, as described above.

According to the present invention, the light-emitting device is intended to lie against a patient's cheek. This means in particular that the size of the illuminating or irradiating surface of the light-emitting device will be adapted to the size of a normal cheek. According to the present invention, the drive means 8, 9, 10 and the light-emitting device 1 are adapted to emit solely infrared (IR) light in accordance with a series of pulse repetition frequencies, where light with a pulse repetition frequency of about 7.8 Hz is emitted first and followed by light that has a pulse repetition frequency of about 287 Hz, which is followed by light that has a pulse repetition frequency of about 31.2 Hz.

The ideal pulse repetition frequencies are 7.8 Hz, 287 Hz and 31.2 Hz respectively, although small deviations are acceptable.

An apparatus constructed solely for treatment of the oral cavity, and particularly for treating gingivitis and pariedontitis may thus have a light-emitting device that is adapted to emit solely infrared light. However, in addition to said light treatment it is conceivable to treat a patient with additional one or more types of monochromatic light either before or after administering said light treatment.

According to one preferred embodiment, the drive means 8, 9, 10 and the light-emitting device 1 are adapted to emit said light for a duration of about 60 to 120 seconds with each pulse repetition frequency. This duration will preferably be about 90 seconds per pulse repetition frequency.

Treatment will thus be administered over a period of only some few minutes. The treatment is repeated on sequential occasions until the intended effect has been achieved.

According to another preferred embodiment, the infrared light has a wavelength of generally about 956 nanometers.

As mentioned in the introduction, it has been found that external treatment on the cheek of a patient in accordance with the present invention significantly palliates and cures gingivitis and pariedontitis despite the fact that the light-emitting device is not directed immediately onto the gums of a patient or placed against the gums. This is thought to be due to the influence of the light on the cheek tissues, which, in turn, influences the tissues around and in the gums.

Regarding gingivitis a pilot study has been made at Tandläkarhögskolan (the College of Dentistry), Huddinge, Sweden including eight patients. Four of them were actively treated in accordance with the present invention, and four of them received ineffective treatment. In the placebo group no changes were observed, but in the group that was treated in accordance with the invention improvements were observed, being of a magnitude which is clinically relevant regarding gingival index (41%), bleeding index (35%) and plaque index (41%).

Regarding pariedontitis a pilot study has been made at Kliniken för tandlossningssjukdomar (the Clinic of Pariedontitis), Malmöhus Iäns Iandsting, Malmö, Sweden including six seriously injured patients, who previously have received two consecutive basic treatments of non-surgical subgingival depuration, but no subsequent healing could be measured. All patients were treated in accordance with the present invention. When following up the results three months [the] later the soundable pocket depth had decreased 33%. Patients who simultaneously had taken vitamin-mineral preparations showed better improvements than the others.

In two cases of pariedontitis, of which the documentation is adequate, a treatment in accordance with the present invention has given favorable results. Scheduled extractions had to be cancelled and swaying teeth have become stable.

Although the invention has been described above with reference to exemplifying embodiments thereof, it will be understood that the invention can be modified with respect to the structural design of the light-emitting device and possible treatment with other types of light.

It will therefore be understood that the present invention is not restricted to the aforedescribed embodiments bit that modifications and variations can be made within the scope of the accompanying claims.

What is claimed is:

1. Apparatus for external medical treatment of the oral cavity with the aid of light, said apparatus comprising: a light-emitting device to be held in close proximity of a patient's oral cavity, wherein the light-emitting device includes light-emitting elements that emit monochromatic light, means for driving the light-emitting device wherein the drive means drives the light-emitting device to emit at least one type of monochromatic light over at least one predetermined time period and to pulsate the light emitted in accordance with a predetermined series of pulse frequencies over said at least one time period, wherein said drive means includes a computer and circuits for driving the light-emitting diodes, wherein the computer is adapted to deliver electric signals to the drive circuits so that the light-emitting diodes emit infrared light within predetermined time periods and at predetermined pulse repetition frequencies, wherein the light emitting device is placed against the patient's cheek, and the drive means drives the light-emitting device to emit solely infrared (IR) light in accordance with a series of pulse repetition frequencies, wherein light that has a pulse repetition frequency of about 7.8 Hz is emitted first and is followed by light that has a pulse repetition frequency of about 287 Hz, which is followed by light that has a pulse repetition frequency of about 31.2 Hz.

2. Apparatus according to claim 1, wherein the drive means and the light-emitting device emit said light for a duration of about 60 to 120 seconds per pulse repetition frequency.

3. Apparatus according to claim 1, wherein the infrared light has a wavelength of about 956 nanometers.

4. Apparatus according to claim 1, wherein the light-emitting elements are light-emitting diodes.

5. A method for external medical treatment of the oral cavity with the aid of light in which a light-emitting device is held in close proximity to a patient's body, which device is adapted to emit at least one type of monochromatic light over one or more predetermined time periods and to pulsate the light emitted in accordance with a predetermined pulse frequency or series of pulse frequencies over said time periods, said method comprising the steps of: placing a light-emitting device against the patient's cheek, and controlling the light-emitting device to emit solely infrared (IR) light in accordance with a series of pulse repetition frequencies, wherein light that has a pulse frequency of about 7.8 Hz is emitted first, and is followed by light that has a pulse repetition frequency of about 287 Hz, which is followed by light that has a pulse repetition frequency of about 31.2 Hz.

6. Method according to claim 5, wherein the light-emitting device emits said light for a duration of about 60 to 120 seconds per pulse repetition frequency.

7. Method according to claim 5, wherein the infrared light has a wavelength of about 956 nanometers.

* * * * *